US012800460B2

(12) United States Patent
Sumiya et al.

(10) Patent No.: US 12,800,460 B2
(45) Date of Patent: Nov. 17, 2026

(54) CONTACTOR AND EVALUATION METHOD OF MINUTE ABRASION CHARACTERISTIC OF MONOCRYSTALLINE DIAMOND USING THE SAME

(71) Applicant: SUMITOMO ELECTRIC INDUSTRIES, LTD., Osaka (JP)

(72) Inventors: Hitoshi Sumiya, Osaka (JP); Yutaka Kobayashi, Osaka (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 265 days.

(21) Appl. No.: 18/707,428

(22) PCT Filed: Oct. 13, 2022

(86) PCT No.: PCT/JP2022/038189
§ 371 (c)(1),
(2) Date: May 3, 2024

(87) PCT Pub. No.: WO2023/084987
PCT Pub. Date: May 19, 2023

(65) Prior Publication Data

US 2025/0035524 A1 Jan. 30, 2025

(30) Foreign Application Priority Data

Nov. 10, 2021 (JP) ................................ 2021-183405

(51) Int. Cl.
*G01N 3/56* (2006.01)
*G01N 33/00* (2006.01)

(52) U.S. Cl.
CPC ............. *G01N 3/56* (2013.01); *G01N 33/389* (2024.05)

(58) Field of Classification Search
CPC .............................. G01N 3/56; G01N 33/389
See application file for complete search history.

(56) References Cited

U.S. PATENT DOCUMENTS

2011/0132954 A1 6/2011 Tomei et al.
2011/0146372 A1 6/2011 Reese et al.
(Continued)

FOREIGN PATENT DOCUMENTS

CN 105158098 A 12/2015
EP 3015236 A1 5/2016
(Continued)

OTHER PUBLICATIONS

Wilks, Eileen M. et al., The Resistance of Diamond to Abrasion, Philosophical Magazine, (1959), 4:38, 158-170, DOI: 10.1080/14786435908243252. (cited in specification).
(Continued)

*Primary Examiner* — Kristina M Deherrera
*Assistant Examiner* — Jean F Morello
(74) *Attorney, Agent, or Firm* — Renner, Otto, Boisselle & Sklar LLP

(57) ABSTRACT

A contactor made of a polycrystalline diamond, being configured to have a rotational axis through the center thereof, comprising a first portion having an inner end portion and a constant thickness in the radial direction, and a second portion having an outer end portion and a decreased thickness in the radial direction; the second portion has a first surface and a second surface continuous with the first portion, and a connection surface connecting the first and second surfaces; the angle θ formed by the first surface and the second surface is 100-150°; the length between a first boundary between the first surface and the connection surface and a second boundary portion between the second surface and the connection surface is 1-10 μm; the length from the rotational axis to the outer end portion is 1-10 mm; and the average particle diameter of diamond particles is 0.1-100 μm.

7 Claims, 7 Drawing Sheets

(56) References Cited

U.S. PATENT DOCUMENTS

| | | | |
|---|---|---|---|
| 2012/0312141 | A1 | 12/2012 | Tomei |
| 2015/0274535 | A1 | 10/2015 | Sato et al. |

FOREIGN PATENT DOCUMENTS

| | | | |
|---|---|---|---|
| JP | 2014-091661 | A | 5/2014 |
| WO | 2019/069888 | A1 | 4/2019 |

OTHER PUBLICATIONS

Wilks E M et al., "The resistance of diamond to abrasion", Journal of Physics D: Applied Physics, (1972), vol. 5, 1902-1919. (cited in specification).

Lee, Masakazu et al., Wear characteristics of various diamonds, non-official translation (Lecture Proceedings of Academic Lecture Conference of 2019 JSPE Spring Conference) Mar. 13, 2019, pp. 646, 647, Internet: <URL: https://doi.org/10.11522/pscjspe.2019S.0_646>, (No English Translation or counterpart available. See concurrently cited International Search Report for corresponding Application No. PCT/JP2022/038189, mailed Nov. 29, 2022, for concise explanation of relevance).

International Search Report for corresponding Application No. PCT/JP2022/038189, mailed Nov. 29, 2022, with Machine Translation.

CONTACTOR AND EVALUATION METHOD OF MINUTE ABRASION CHARACTERISTIC OF MONOCRYSTALLINE DIAMOND USING THE SAME

TECHNICAL FIELD

The present disclosure relates to a contactor and an evaluation method of a minute abrasion characteristic of monocrystalline diamond using the contactor. This application claims priority based on Japanese Patent Application No. 2021-183405 filed on Nov. 10, 2021, and the entire contents of the Japanese patent application are incorporated herein by reference.

BACKGROUND ART

In industrial monocrystalline diamond, the nitrogen impurity and the distribution state of crystal defects differ from crystal to crystal, and even in the same crystal, the abrasion characteristic differ from region to region in the minute region. Therefore, particularly when using monocrystalline diamond as a tool material for precision machining, it is important to sufficiently understand the difference in abrasion characteristics between minute regions in the same crystal.

In order to evaluate the abrasion characteristic of the minute region of monocrystalline diamond, a method using a cast iron wheel or a metal bond diamond grinding wheel having a small diameter and a V-shaped cutting edge is known (Non-patent literature 1, Non-patent literature 2).

CITATION LIST

Non Patent Literature

Non-patent literature 1: Eileen M. Wilks&J. Wilks. (1959). "The Resistance of Diamond to Abrasion". Philosophical. Magazine, 4:38, 158-170.

Non-patent literature 2: E M Wilks and J Wilks. (1972). "The resistance of diamond to abrasion". Journal of Physics D: Applied Physics, 5, 1902-1919.

SUMMARY OF INVENTION

The contactor of the present disclosure is a contactor having an annular shape and made of a polycrystalline diamond including a plurality of diamond particles, the contactor being configured to have a rotation axis extending through a center of the contactor. The contactor includes, a first portion having a constant thickness in a radial direction, the first portion including an inner end portion, and a second portion having a thickness decreasing in the radial direction, the second portion including an outer end portion. The second portion has a first surface continuous with an upper surface of the first portion, a second surface continuous with a lower surface of the first portion, and a connection surface connecting the first surface and the second surface to each other and including the outer end portion. In a cross-section along the rotation axis, an angle θ formed by a first line segment indicating the first surface and a second line segment indicating the second surface is 100° to 150°, a length between a first boundary portion and a second boundary portion is 1 μm to 10 μm, the first boundary portion being a boundary between the first surface and the connection surface, the second boundary portion being a boundary between the second surface and the connection surface, and a length from the rotation axis to the outer end portion is 1 mm to 10 mm. An average particle diameter of the plurality of diamond particles is 0.1 μm to 100 μm.

The evaluation method of the present disclosure is an evaluation method of an abrasion characteristic of a monocrystalline diamond in a minute region. The evaluation method incudes, forming an abrasion mark on the monocrystalline diamond by, while rotating the contactor, pressing the monocrystalline diamond against the outer end portion of the contactor, and evaluating the abrasion characteristic of the monocrystalline diamond in the minute region based on a length of the abrasion mark.

DETAILED DESCRIPTION

Figure 1:
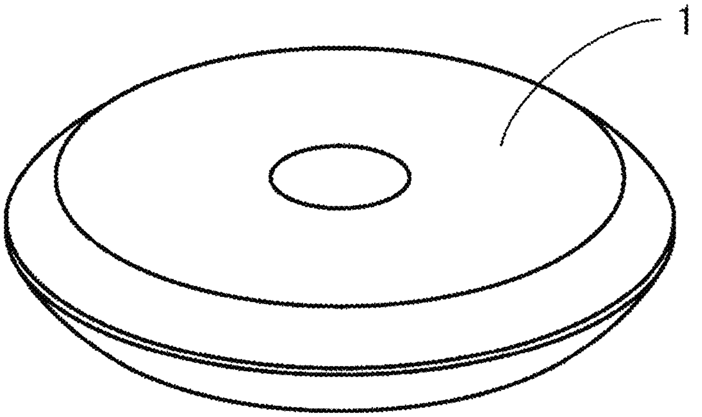
FIG. 1 is a diagram showing an appearance of an example of a contactor according to an embodiment of the present disclosure.

Problems to be Solved by the Present Disclosure

The cast iron wheel described in Non-patent literature 1 is soft with respect to the monocrystalline diamond, and therefore, the cutting edge is likely to lose its shape during the abrasion test, and no abrasion mark is formed depending on the abrasion direction. Further, diamond powder of the abrasive is scattered, and the sharpness is quickly reduced. Therefore, it is difficult to quantitatively and appropriately evaluate the abrasion characteristic in the minute region of the monocrystalline diamond.

When the metal bond diamond grinding wheel described in Non-patent literature 2 is used for a monocrystalline diamond material, diamond abrasive grains are likely to fall off, and the cutting edge is likely to lose its shape. In addition, due to the variation in the grain size and strength of the diamond abrasive grain, the grinding performance of the cutting edge is not stable. Therefore, it is difficult to quantitatively and appropriately evaluate the abrasion characteristic in the minute region of the monocrystalline diamond.

Therefore, an object of the present disclosure is to provide a contactor used in an evaluation method of an abrasion characteristic in a minute region of a monocrystalline diamond and an evaluation method of an abrasion characteristic in the minute region of the monocrystalline diamond using the same.

Effects of Present Disclosure

According to the present disclosure, it is possible to provide a contactor used in the evaluation method of the abrasion characteristic in a minute region of monocrystalline diamond. Further, it is possible to evaluate the abrasion characteristic in the minute region of the monocrystalline diamond by using the contactor.

DESCRIPTION OF EMBODIMENTS OF PRESENT DISCLOSURE

First, embodiments of the present disclosure will be listed and described.

(1) The contactor of the present disclosure is a contactor having an annular shape and made of a polycrystalline diamond including a plurality of diamond particles, the contactor being configured to have a rotation axis extending through a center of the contactor. The contactor includes, a first portion having a constant thickness in a radial direction, the first portion including an inner end portion, and a second portion having a thickness decreasing in the radial direction, the second portion including an outer end portion. The second portion has a first surface continuous with an upper surface of the first portion, a second surface continuous with a lower surface of the first portion, and a connection surface connecting the first surface and the second surface to each other and including the outer end portion. In a cross-section along the rotation axis, the angle $\theta$ formed by a first line segment indicating the first surface and a second line segment indicating the second surface is 1000 to 150°, a length between a first boundary portion and a second boundary portion is 1 µm to 10 µm, the first boundary portion being a boundary between the first surface and the connection surface, the second boundary portion being a boundary between the second surface and the connection surface, and a length from the rotation axis to the outer end portion is 1 mm to 10 mm. An average particle diameter of the plurality of diamond particles is 0.1 µm to 100 µm.

According to the present disclosure, the abrasion characteristic in the minute region of the monocrystalline diamond (in the present description, the abrasion characteristic in the minute region is also referred to as "minute abrasion characteristic") is described as follows.

(2) The Knoop hardness of the polycrystalline diamond may be 45 GPa or more. According to this, the accuracy of the evaluation of the minute abrasion characteristic is improved.

(3) A line of intersection of the connection surface and a cross-section including the rotation axis may be a straight line. According to this, the evaluation result of the minute abrasion characteristic is stabilized.

(4) The length from the rotation axis to the outer end portion may be larger than a length from the rotation axis to the first boundary portion and larger than a length from the rotation axis to the second boundary portion. According to this, the evaluation result of the minute abrasion characteristic is stabilized.

(5) The evaluation method of the present disclosure is an evaluation method of an abrasion characteristic of a monocrystalline diamond in a minute region. The evaluation method incudes, a first step of forming an abrasion mark on the monocrystalline diamond by, while rotating the contactor, pressing the monocrystalline diamond against the outer end portion of the contactor, and a second step of evaluating the abrasion characteristic of the monocrystalline diamond in the minute region based on a length of the abrasion mark.

According to the present disclosure, it is possible to evaluate the abrasion characteristic in the minute region of the monocrystalline diamond.

(6) The monocrystalline diamond may have a plane. The first step of forming may include, a 1-1 step of disposing the monocrystalline diamond with the plane facing the contactor and being parallel to the rotation axis, and a 1-2 step of pressing the monocrystalline diamond against the outer end portion by applying a load in a normal direction of the third plane to the monocrystalline diamond.

According to this, the accuracy of the evaluation of the minute abrasion characteristic is improved.

(7) The plane of the monocrystalline diamond may be a (001) plane. The abrasion mark may be parallel to a <100> direction of the (001) plane. According to this, the accuracy of the evaluation of the minute abrasion characteristic is improved.

DETAILS OF EMBODIMENTS OF PRESENT DISCLOSURE

Figure 3:
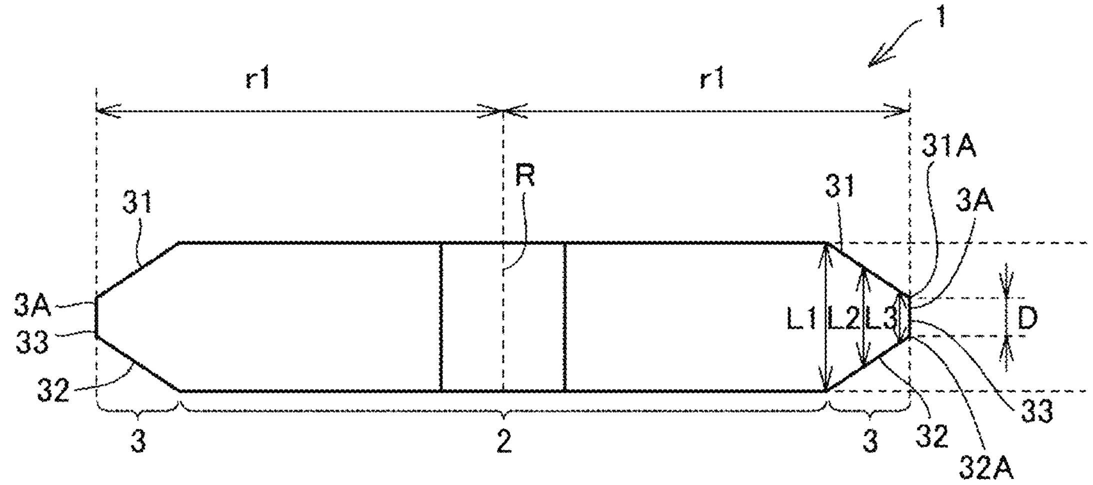
FIG. 3 is a XI-XI-line cross-sectional view of the contactor shown in FIG. 2.
Figure 4:
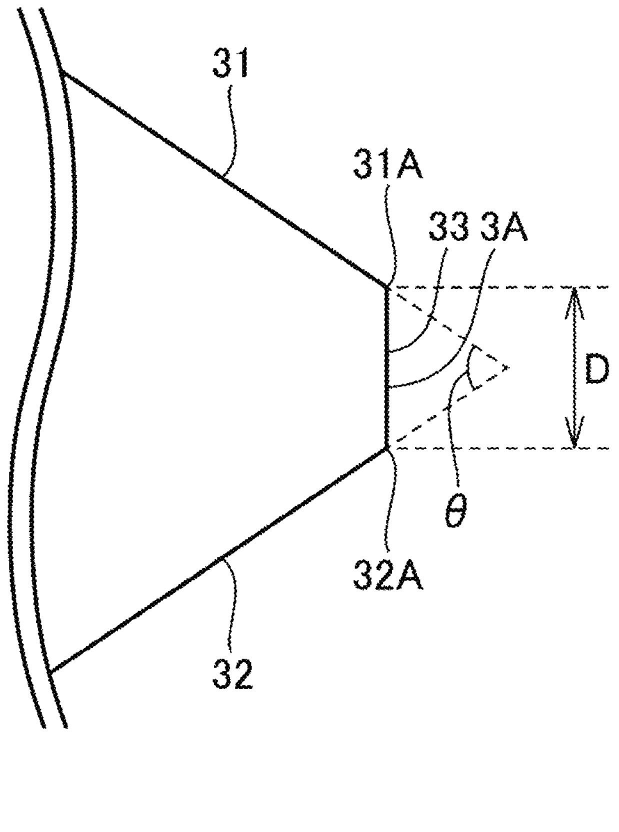
FIG. 4 is an enlarged view of the second portion of the contactor shown in FIG. 3.
Figure 5:
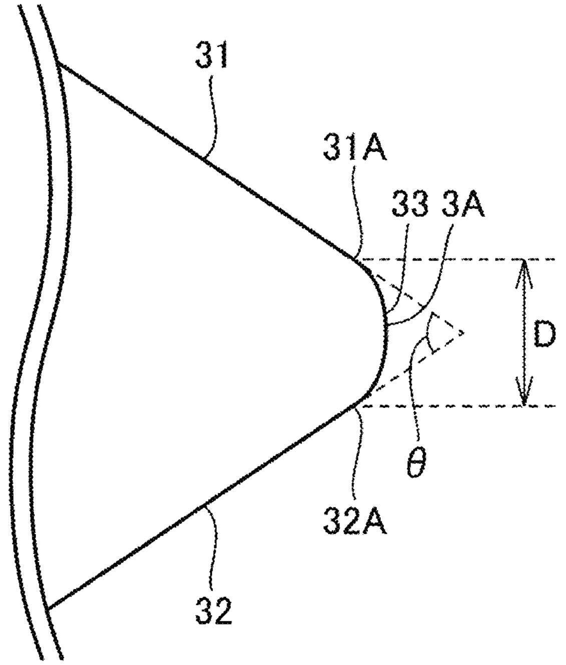
FIG. 5 is a cross-sectional view of a second portion in accordance with another embodiment of the present disclosure.

The contactor of the present disclosure and the evaluation method of the minute abrasion characteristic of monocrystalline diamond using the contactor will be described below with reference to the drawings. In the drawings of the present disclosure, the same reference numerals denote the same or corresponding parts. In addition, the dimensional relationships such as length, width, thickness, and depth are appropriately changed for the sake of clarity and simplification of the drawings, and do not necessarily represent the actual dimensional relationships. It is noted that, for convenience of explanation, FIGS. 3, 4, and 5 are compressed in the vertical direction.

In the present description, the notation in the form of "A to B" means the upper limit and the lower limit of the range (that is, A or more and B or less), and in a case where a unit is not described in A and a unit is described only in B, the unit of A and the unit of B are the same.

Regarding crystallographic denotation in the present description, a group orientation is shown in < > and an individual plane is shown in ( ), respectively.

In the present description, the step of forming the abrasion mark on the monocrystalline diamond using the contactor, which is performed for evaluation of the minute abrasion characteristic of the monocrystalline diamond, is also referred to as an abrasion test.

Embodiment 1: Contactor

The contactor of an embodiment of the present disclosure (hereinafter also referred to as "the embodiment") will be described with reference to FIG. 1 to FIG. 5. A contactor 1 of the embodiment is a contactor having an annular shape and made of a polycrystalline diamond including a plurality of diamond particles, the contactor being configured to have a rotation axis R extending through a center of the contactor. Contactor 1 includes, a first portion 2 having a constant thickness in a radial direction, first portion 2 including an inner end portion, and a second portion 3 having a thickness decreasing in the radial direction, second portion 3 including an outer end portion 3A. Second portion 3 has a first surface 31 continuous with an upper surface of first portion 2, a second surface 32 continuous with a lower surface of first portion 2, and a connection surface 33 connecting first surface 31 and second surface 32 to each other and including outer end portion 3A. In a cross-section along rotation axis R, the angle θ formed by a first line segment indicating first surface 31 and a second line segment indicating second surface 32 is 100° to 150°, a length between a first boundary portion 31A and a second boundary portion 32A is 1 μm to 10 μm, first boundary portion 31A being a boundary between first surface 31 and connection surface 33, second boundary portion 32A being a boundary between second surface 32 and connection surface 33, and a length from rotation axis R to outer end portion 3A is 1 mm to 10 mm. An average particle diameter of the plurality of diamond particles is 0.1 μm to 100 μm.

The contactor of the present embodiment is made of a polycrystalline diamond including a plurality of diamond particles. The polycrystalline diamond may include a plurality of diamond particles and a binder. The polycrystalline diamond may be made of a plurality of diamond particles and a binder. As the binder, at least one selected from the group consisting of cobalt (Co), nickel (Ni), and iron (Fe) can be used. The polycrystalline diamond may include a sintering aid such as WC or SiC. Alternatively, polycrystalline diamond from which the binder and sintering aid have been removed by acid treatment or the like may be used.

The lower limit of the content of the diamond component in the polycrystalline diamond may be 80 vol % or more, 83 vol % or more, or 85 vol % or more. The upper limit of the content of the diamond component in the polycrystalline diamond may be 99.9 vol % or less, 99 vol % or less, or 98 vol % or less. The content of the diamond component in the polycrystalline diamond may be 80 vol % to 99.9 vol %, 83 vol % to 99 vol %, or 85 vol % to 98 vol %. The content of the volume base of the diamond component in the polycrystalline diamond can be confirmed by an X-ray diffraction method. Specifically, the crystallite size can be calculated from the intensity ratio between the diffraction peak of the diamond and the diffraction peak of the binder.

The lower limit of the content of the binder in the polycrystalline diamond may be 0.1 vol % or more, 1 vol % or more, or 2 vol % or more. The upper limit of the content of the binder in the polycrystalline diamond may be 20 vol % or less, 18 vol % or less, 17 vol % or less, or 15 vol % or less. The content of the binder in the polycrystalline diamond may be 0.1 vol % to 20 vol %, 1 vol % to 18 vol %, 1 vol % to 17 vol %, or 2 vol % to 15 vol %. The content of the volume base of the binder in the polycrystalline diamond can be confirmed by the X-ray diffraction method. Specifically, the crystallite size can be calculated from the intensity ratio of the diffraction peak of the diamond to the diffraction peak of the binder. The composition of the binder can be confirmed by X-ray diffraction.

The polycrystalline diamond may include a diamond component, a binder, and inevitable impurities. The polycrystalline diamond may consist of a diamond component, a binder, and inevitable impurities. The polycrystalline diamond may include 80 vol % to 99.9 vol % of a diamond component and 0.1 vol % to 20 vol % of a binder. The polycrystalline diamond may include 83 vol % to 99 vol % of a diamond component and 1 vol % to 17 vol % of a binder. The polycrystalline diamond may include 85 vol % to 98 vol % of a diamond component and 2 vol % to 15 vol % of a binder.

In the polycrystalline diamond, diamond particles may be directly bonded to each other. For example, diamond particles may be strongly bonded to each other through neck growth. According to this, the outer end portion is further prevented from losing its shape due to the use of the contactor, and the lifespan of the contactor is improved.

The average particle diameter of a plurality of diamond particles included in the polycrystalline diamond (hereinafter, also referred to as "average particle diameter of diamond particles") is 0.1 μm to 100 μm. The hardness of the polycrystalline diamond has no orientation dependency, and the polycrystalline diamond has high strength.

The lower limit of the average particle diameter of the diamond particles is 0.1 μm or more. This can provide a mechanical strength characteristic of diamond. In addition, since a large number of irregularities of about 0.1 μm to 1 μm are formed on the surface of the polycrystalline diamond, in an abrasion test using the contactor made of the polycrystalline diamond, the contactor satisfactorily bites into the monocrystalline diamond, and thus a stable abrasion test can be performed. The lower limit of the average particle diameter of the diamond particles is 0.1 μm or more, and can be 1 μm or more, 3 μm or more, 5 μm or more, 7 μm or more, 10 μm or more, or 20 μm or more. The upper limit of the average particle diameter of the diamond particles is 100 μm or less, and can be 90 μm or less, 80 μm or less, 70 μm or less, 50 μm or less, 30 μm or less, 10 μm or less, 5 μm or less, or 3 μm or less, from the viewpoint that the polycrystalline diamond can exhibit isotropic hardness and abrasion resistance with respect to all orientations. The average particle diameter of the diamond particles is 0.1 μm to 100 μm, and can be 0.1 μm to 100 μm, 0.1 μm to 90 μm, 0.1 μm to 80 μm, 0.1 μm to 70 μm, 0.1 μm to 50 μm, 0.1 μm to 30 μm, 0.1 μm to 10 μm, 0.1 μm to 5 μm, 0.1 μm to 3 μm, 1 μm to 100 μm, 1 μm to 90 μm, 1 μm to 80 μm, 1 μm to 70 μm, 1 μm to 50 μm, 1 μm to 30 μm, 1 μm to 10 μm, 1 μm to 5 μm, 1 μm to 3 μm, 3 μm to 100 μm, 3 μm to 90 μm, 3 μm to 80 μm, 3 μm to 70 μm, 3 μm to 50 μm, 3 μm to 30 μm, 3 μm to 10 μm, 3 μm to 5 μm, 7 μm to 100 μm, 7 μm to 90 μm, 7 μm to 80 μm, 7 μm to 70 μm, 7 μm to 50 μm, 7 μm to 30 μm, 7 μm to 10 μm, 10 μm to 100 μm, 10 μm to 90 μm, 10 μm to 80 μm, 10 μm to 70 μm, 10 μm to 50 μm, 10 μm to 30 μm, 20 μm to 100 μm, 20 μm to 90 μm, 20 μm to 80 μm, 20 μm to 70 μm, 20 μm to 50 μm, or 20 μm to 30 μm.

The average particle diameter of the diamond particles is determined by a cutting method using a scanning electron microscope (SEM). Specifically, first, the polycrystalline diamond is observed at a magnification of 1,000 to 100,000 times using the scanning electron microscope to obtain an SEM image.

Next, a circle is drawn on the SEM image, and eight straight lines are drawn radially from the center of the circle (so that the intersection angles between the straight lines are substantially equal) to the outer circumference of the circle. In this case, the observation magnification and the diameter of the circle are set such that the number of diamond particles (crystal particles) crossed by one straight line is about 10 to 50.

Next, the number of diamond particles crossing the crystal grain boundary is counted for each straight line, the length of the straight line is divided by the number of crossings to obtain the average intercept length, and the average intercept length is multiplied by 1.128 to obtain the average particle diameter. The above measurement is performed on three SEM images, and the average particle diameter is obtained for each of the three SEM images. The average value of the average particle diameters of the three SEM images is defined as the average particle diameter of the diamond particle in the present description.

It was confirmed that, as far as the measure is concerned, the measurement results hardly vary even when the measurement was performed a plurality of times by changing the selected portion of the measurement visual field, and the measurement visual field does not become arbitrary even when the measurement visual field is set at random.

When the abrasion characteristic in the minute region of the monocrystalline diamond is evaluated using contactor 1, outer end portion 3A of contactor 1 is brought into contact with the monocrystalline diamond while rotating contactor 1 around rotation axis R as a center, and an abrasion mark is formed on the monocrystalline diamond. Therefore, the polycrystalline diamond included in the contactor of the present embodiment may have a hardness and a structure (voids) that can cause a monocrystalline diamond 75 to form abrasion marks.

The hardness of monocrystalline diamond 75 varies from 70 GPa to 120 GPa depending on the plane orientation. Therefore, the Knoop hardness of the polycrystalline diamond is preferably 45 GPa or more, and a large number of irregularities of 0.1 μm or more are preferably formed on the contactor surfaces. According to this, in the abrasion test, contactor 1 satisfactorily bites into monocrystalline diamond 75, and thus the stable abrasion test can be performed. In addition, the surface of monocrystalline diamond 75 can be ground by the high-hardness plane orientation of the monocrystalline diamond particles exposed on the surface in the irregularities of contactor 1. The Knoop hardness of the polycrystalline diamond may be 45 GPa or more, 50 GPa or more, or 60 GPa or more. The upper limit of the Knoop hardness of the polycrystalline diamond is not particularly limited, but may be 100 GPa or less from the viewpoint of production. The Knoop hardness of the polycrystalline diamond can be 45 GPa to 100 GPa, 50 GPa to 100 GPa, 60 GPa to 100 GPa, 45 GPa to 90 GPa, 50 GPa to 90 GPa, and 60 GPa to 80 GPa.

In the present description, the Knoop hardness of the polycrystalline diamond is measured under the conditions defined in JIS Z 2251:2009. In particular, a rhombic Knoop indenter is pressed into the polycrystalline diamond surface to apply a load for 10 seconds with a test force of 4.9 N, thereby forming an indentation. The test temperature is 23° C.±5° C. After the test force is released, the length a (μm) of the longer diagonal line of the indentation remaining on the surface of the polycrystalline diamond is measured, and the Knoop hardness (HK) is calculated from the following Equation (1).

$$HK = 14229 \times F/a^2 \qquad \text{Equation (1)}$$

Figure 2:
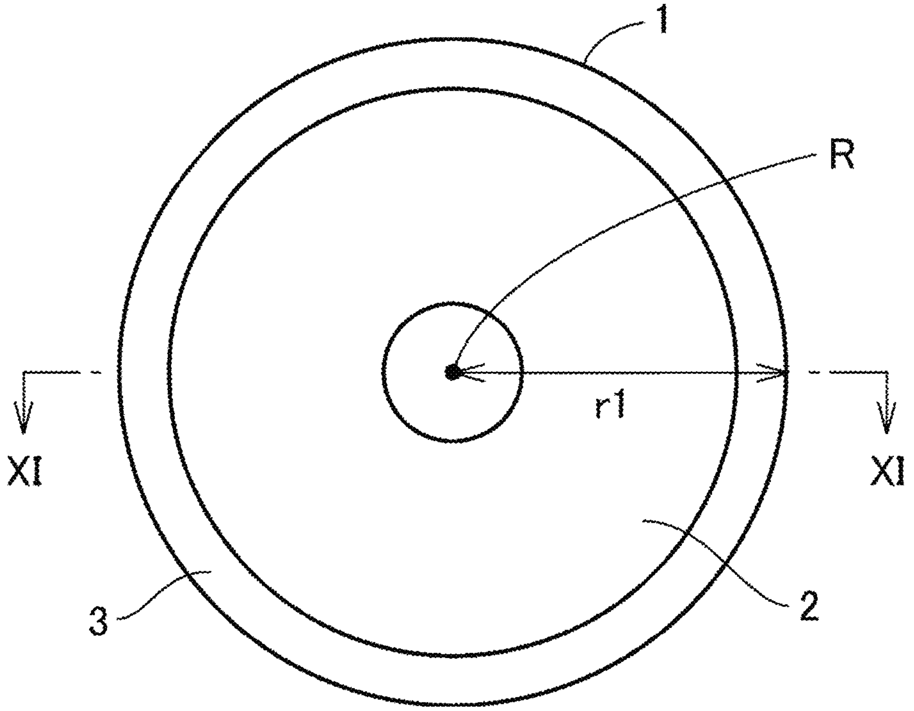
FIG. 2 is a top view of an example of a contactor in accordance with an embodiment of the present disclosure.

As shown in FIG. 1 to FIG. 3, contactor 1 includes first portion 2 and second portion 3 that is continuous with first portion 2 and surrounds the outer circumference of first portion 2, and in a cross-section including rotation axis R, the length of second portion 3 in rotation axis R direction decreases toward outer end portion 3A. Here, the length of rotation axis R direction of second portion 3 decreasing toward outer end portion 3A means that, as shown in FIG. 3, when the length of rotation axis R direction of second portion 3 is L1, L2, and L3 in order of closeness to the rotation axis, the relationship L1>L2>L3 is satisfied. The maximum length of contactor 1 in rotation axis R direction is not particularly limited, but can be set to, for example, 0.5 mm to 5 mm.

As shown in FIG. 2, contactor 1 is a circular shape in top view. A length r1 in a direction orthogonal to rotation axis R between rotation axis R of contactor 1 and outer end portion 3A is 1 mm to 10 mm. According to this, contactor 1 can be easily handled, and the minute abrasion mark can be formed on monocrystalline diamond 75.

The lower limit of the length r1 is 1 mm or more, and can be set to be 2 mm or more, or 3 mm or more, from the viewpoint of ease of handling of contactor 1. The upper limit of the length r1 is 10 mm or less, and can be 7 mm or less, 5 mm or less, 3 mm or less, or 2 mm or less, from the viewpoint of forming a minute abrasion mark. The length r1 is 1 mm to 10 mm, and can be 2 mm to 10 mm, 3 mm to 10 mm, 1 mm to 7 mm, 2 mm to 7 mm, 3 mm to 7 mm, 1 mm to 5 mm, 2 mm to 5 mm, 3 mm to 5 mm, 1 mm to 3 mm, and 1 mm to 2 mm.

The angle θ of contactor 1 formed by first surface 31 and second surface 32 is 1000 to 150°, a length D in rotation axis R direction between first boundary portion 31A and second boundary portion 32A is 1 μm to 10 μm. First boundary portion 31A is a boundary between first surface 31 and connection surface 33. Second boundary portion 32A is a boundary between second surface 32 and connection surface 33. In the present description, the angle θ formed by first surface 31 and second surface 32 means an angle formed by virtual planes obtained by enlarging first surface 31 and second surface 32 as indicated by a dotted line in FIG. 4. According to this, the abrasion mark formed on the monocrystalline diamond becomes clear, and a stable abrasion test can be performed. Therefore, the variation in the evaluation result of the minute abrasion characteristic is suppressed, and the evaluation result is stabilized.

The lower limit of the angle θ may be 100° or more, or may be 110° or more, from the viewpoint of maintaining the shape of the outer end portion (cutting edge) during the abrasion test. The upper limit of the angle θ may be 150° or less, or may be 140° or less, from the viewpoint of forming a clear abrasion mark. The angle θ may be 100° to 150°, or may be 110° to 140°.

The lower limit of the length D may be 1 μm or more, or may be 2 μm or more, from the viewpoint of maintaining the shape of an outer end portion (cutting edge) during the abrasion test. The upper limit of the length D may be 10 μm or less, or may be 8 μm or less, from the viewpoint of forming a clear abrasion mark. The length D may be 1 μm to 10 μm, or may be 2 μm to 8 μm.

As shown in FIG. 4, the line of intersection between connection surface 33 and the cross-section including rotation axis R may be a straight line. According to this, a stable abrasion test can be performed. Therefore, the variation in the evaluation result of the minute abrasion characteristic is suppressed, and the evaluation result is stabilized.

As shown in FIG. 5, the length from rotation axis R to outer end portion 3A may be larger than the length from rotation axis R to first boundary portion 31A and larger than the length from rotation axis R to second boundary portion 32A. This enables a stable abrasion test. Therefore, the variation in the evaluation result of the minute abrasion characteristic is suppressed, and the evaluation result is stabilized. In the case where connection surface 33 is an arc in the cross-section including rotation axis R, the radius of the arc is preferably 1 μm to 10 μm, more preferably 2 μm to 8 μm.

As shown in FIG. 1 to FIG. 3, first portion 2 of contactor 1 preferably includes a hole formed in a portion corresponding to rotation axis R. According to this, in the abrasion test, a spindle can be inserted into the hole. In addition, contactor 1 may include a shaft fixed to first portion 2.

An example of a method of manufacturing the contactor of the present embodiment will be described. The polycrystalline diamond is synthesized by mixing diamond powder and Co powder as a raw material of a binder at a predetermined ratio, filling the mixture in a capsule of cemented carbide or high-melting point metal, and sintering the mixture under high pressure and high temperature. The sintering conditions can be, for example, a temperature of 1300 to 1600° C., a pressure of 5 to 6 GPa, and a sintering time of 1 to 30 minutes. The obtained polycrystalline diamond is formed into the shape of the contactor of the present embodiment by grinding and polishing with a diamond grinding wheel or by electric discharge to obtain the contactor.

The polycrystalline diamond synthesized by the above method is relatively inexpensive and easy to process. Therefore, the contactor obtained by the above method is advantageous in terms of cost.

Figure 6:
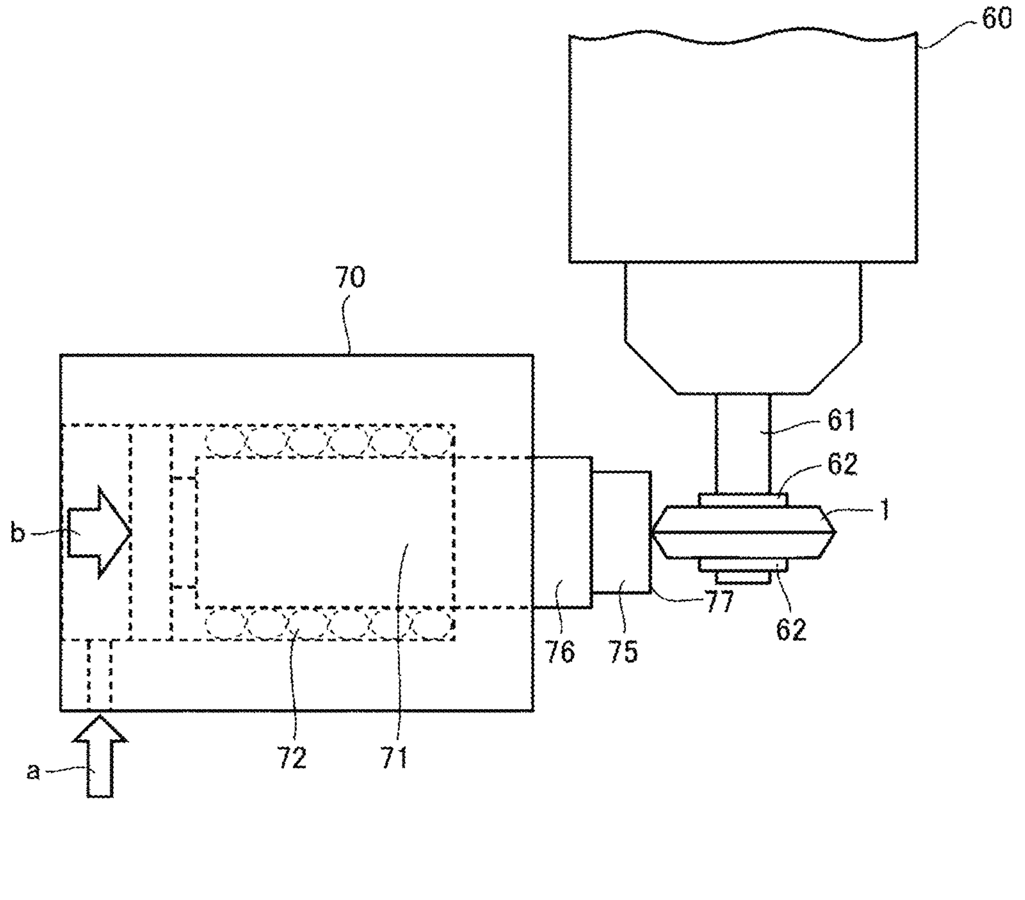
FIG. 6 is a schematic view of an abrasion testing apparatus used in the evaluation method of an abrasion characteristic in a minute region of a monocrystalline diamond according to an embodiment of the present disclosure.

Embodiment 2: Evaluation Method of Abrasion Characteristic in Minute Region of Monocrystalline Diamond The evaluation method of the abrasion characteristic in the minute region of the monocrystalline diamond of the present embodiment will be described with reference to FIG. 6. FIG. 6 is a schematic view of an abrasion testing apparatus used in the method of evaluating the minute abrasion characteristic according to the present embodiment. The abrasion testing apparatus includes a machining center 60 and a sample holding portion 70. Machining center 60 includes a spindle 61 and a fixation screw 62 for fixing contactor 1 to spindle 61. Sample holding portion 70 includes a jig 76 for holding monocrystalline diamond 75, an air cylinder 71 for moving jig 76 in a contactor 1 direction, and a linear guide 72 disposed around air cylinder 71.

The evaluation method of an abrasion characteristic of monocrystalline diamond 75 in a minute region of the present disclosure incudes, a first step of forming an abrasion mark on monocrystalline diamond 75 by, while rotating contactor 1 according to the embodiment 1, pressing monocrystalline diamond 75 against outer end portion 3A of contactor 1, and a second step of evaluating the abrasion characteristic of monocrystalline diamond 75 in the minute region based on a length of the abrasion mark.

<First Step>

Spindle 61 of machining center 60 is inserted into a hole of contactor 1 and fixed by fixation screw 62. Since contactor 1 is fixed to spindle 61, when spindle 61 is rotated, contactor 1 is rotated in synchronization with the rotation of spindle 61. The rotation condition is preferably a rotational number of 100 rpm to 3000 rpm and/or a circumferential speed of 1 m/min to 100 m/min from the viewpoint of suppressing thermal abrasion. In FIG. 6, contactor 1 is fixed to spindle 61 by fixation screw 62, but the method of fixing contactor 1 to spindle 61 is not limited to this. For example, contactor 1 and spindle 61 can be fixed to each other by using an adhesive.

Monocrystalline diamond 75 is fixed to jig 76 of sample holding portion 70. Air cylinder 71 is provided in the direction opposite to the direction in which monocrystalline diamond 75 is fixed to jig 76. As shown by the direction of arrow a in FIG. 6, by sending air of a constant pressure toward air cylinder 71, a load is applied to air cylinder 71 in the direction of arrow b, and air cylinder 71 moves in the direction of contactor 1. As a result, monocrystalline diamond 75 is pressed against outer end portion 3A, and an abrasion mark is formed on monocrystalline diamond 75. The pressing pressure is preferably 0.1 MPa to 0.2 MPa. The pressing time is preferably 1 to 10 minutes.

Monocrystalline diamond 75 may have a plane 77. The first step may include, a 1-1 step of disposing monocrystalline diamond 75 with plane 77 facing contactor 1 and being parallel to rotation axis R, and a 1-2 step of pressing monocrystalline diamond 75 against outer end portion 3A by applying a load in a normal direction of plane 77 to monocrystalline diamond 75. This improves the accuracy of the minute abrasion test. When monocrystalline diamond 75 is processed to have plane 77, the (001) plane of monocrystalline diamond 75 is preferably parallel-polished with a metal bond diamond grinding wheel or a skeif.

Plane 77 of monocrystalline diamond 75 is the (001) plane, and the abrasion mark is preferably parallel to the <100> direction of the (001) plane. This improves the accuracy of the minute abrasion test.

When a plurality of abrasion marks are formed on one monocrystalline diamond 75, the plurality of abrasion marks are preferably substantially parallel to each other, and the abrasion mark interval is preferably 50 μm to 100 μm.

It is noted that, when the first surface and the second surface of the contactor are directly connected to form a V shape and no connection surface is present before the start of the formation of the abrasion mark, the length D of the outer end portion is adjusted to be 1 μm to 10 μm by performing pretreatment five times or more under the above-described conditions (rotational speed, pressing pressure, and pressing time) for forming the abrasion mark in the <100> direction of the (001) plane of the monocrystalline diamond before the formation of the abrasion mark for evaluation.

<Second Step>

In the second step, the abrasion characteristic of the monocrystalline diamond is evaluated based on the length of the abrasion mark formed on the monocrystalline diamond in the first step. The abrasion characteristic can be evaluated by the abrasion amount (removal amount), the area of the abrasion mark, or the length of the abrasion mark. In the present embodiment, evaluation is performed by the length of the abrasion mark which can be easily measured. The length of the abrasion mark is measured with an optical microscope at an observation magnification of 500 times.

The evaluation method of the minute abrasion characteristic according to the present embodiment can evaluate the abrasion characteristic (abrasion resistance) of the minute region of the monocrystalline diamond with high accuracy.

This enables the distribution state of the abrasion characteristic of the monocrystalline diamond due to the uneven distribution of impurities and crystal defects to be investigated in detail. This evaluation method is useful for selection and quality evaluation of monocrystalline diamond when the monocrystalline diamond is used for precision cutting tools such as precision bit and small diameter end mill.

Appendix 1

The contactor of the present embodiment may be made of a polycrystalline diamond including a plurality of diamond particles, and a content of a diamond component of the polycrystalline diamond may be 80 vol % or more.

Appendix 2

The contactor of the present embodiment may be made of a polycrystalline diamond including a plurality of diamond particles, and a content of a diamond component of the polycrystalline diamond may be 80 vol % to 99.9 vol %.

Appendix 3

The contactor of the present embodiment is made of a polycrystalline diamond including a plurality of diamond particles, and the polycrystalline diamond includes a plurality of diamond particles and a binder. A content of a diamond component in the polycrystalline diamond may be 80 vol % to 99.9 vol %, and the polycrystalline diamond may have a binder content of 0.1 vol % to 20 vol %.

Appendix 4

The contactor of the present embodiment is made of a polycrystalline diamond including a plurality of diamond particles, and the polycrystalline diamond is made of a plurality of diamond particles and a binder. A content of a diamond component in the polycrystalline diamond is 80 vol % to 99.9 vol %, and the polycrystalline diamond may have a binder content of 0.1 vol % to 20 vol %.

EXAMPLE

The present embodiment will be described more specifically by examples. However, the present embodiment is not limited to these examples.

In all of the following examples, a plane was formed by parallel polishing the (001) plane of a test piece made of monocrystalline diamond with a metal bond diamond grinding wheel or a skeif plate, and the minute abrasion characteristic was evaluated on the plane.

In all of the following examples, the contactor is made of a polycrystalline diamond including a plurality of diamond particles. The content of the diamond component is 90 vol % and the content of the bonding phase (composition: Co) is 10 vol % in the polycrystalline diamond. The average particle diameter of the plurality of diamond particles is 1 μm. Knoop hardness of the polycrystalline diamond is 50 GPa.

Example 1: Evaluation of Minute Abrasion Characteristic of (001) Plane of Synthetic IIa Type Monocrystalline Diamond in <100> Direction The contactor described in embodiment 1 was prepared as a contactor. The contactor has a cross-section shape shown in FIG. 3, and has the length r1 of 5 mm (a circle with a diameter of y10 mm in top view), the angle θ of 120°, the length D of 1 μm, and a maximum length (thickness) of 5 mm in rotation axis R direction.

Figure 7:
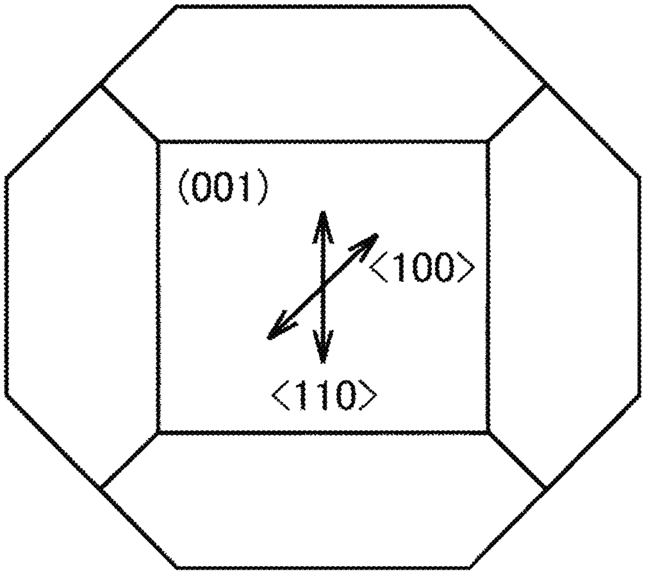
FIG. 7 is a diagram showing the <100> direction and the <110> direction of the (001) plane of the monocrystalline diamond.

The contactor was installed in the abrasion testing apparatus shown in FIG. 6, and as shown in FIG. 7, abrasion marks were formed in parallel in the <100> direction of the (001) plane on a test piece made of synthetic IIa type monocrystalline diamond, and evaluation was performed. The conditions for forming the abrasion mark are rotational number 1000 rpm of the contactor, pressing pressure 0.1 MPa, and pressing time 10 minutes.

Figure 8:
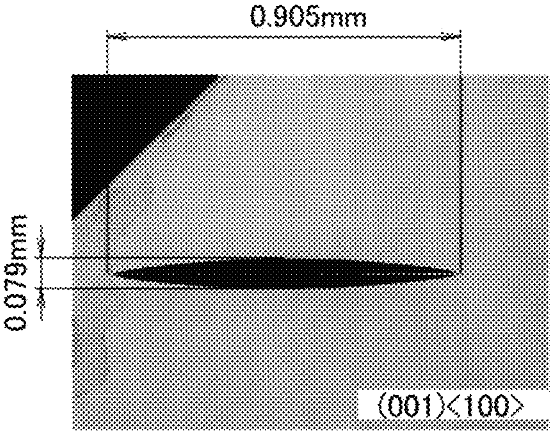
FIG. 8 is a photo substitutional view showing the abrasion mark formed in Example 1.

An optical microscopic image of the formed abrasion mark is shown in FIG. 8. As shown in FIG. 8, according to the present abrasion test, it was confirmed that a clear abrasion mark was formed on the synthetic IIa type monocrystalline diamond.

Example 2: Comparison of Abrasion Characteristic of (001) Plane of Synthetic IIa Monocrystalline Diamond in <110> Direction and <100> Direction The contactor described in embodiment 1 was prepared as a contactor. The contactor has a cross-section shape as shown in FIG. 3, and has the length r1 of 1.6 mm (a circle with a diameter of φ3.2 mm in top view), the angle θ of 120°, and the maximum length (thickness) of 5 mm in rotation axis R direction, except that the outer end portion is V-shaped (that is, the first plane and the second plane intersect to form the angle θ, and connection surface 33 is not present).

The contactor was installed in the abrasion testing apparatus shown in FIG. 6, and abrasion marks were formed in parallel in the <110> direction of the (001) plane and the <100> direction of the (001) plane on a test piece made of synthetic IIa type monocrystalline diamond, and evaluation was performed. The conditions for forming the abrasion mark are: the rotational number 313 rpm of the contactor, pressing pressure 0.1 Mpa, and pressing time 1 minute per abrasion mark. The abrasion mark interval on the test piece was 200 μm.

Figure 9:
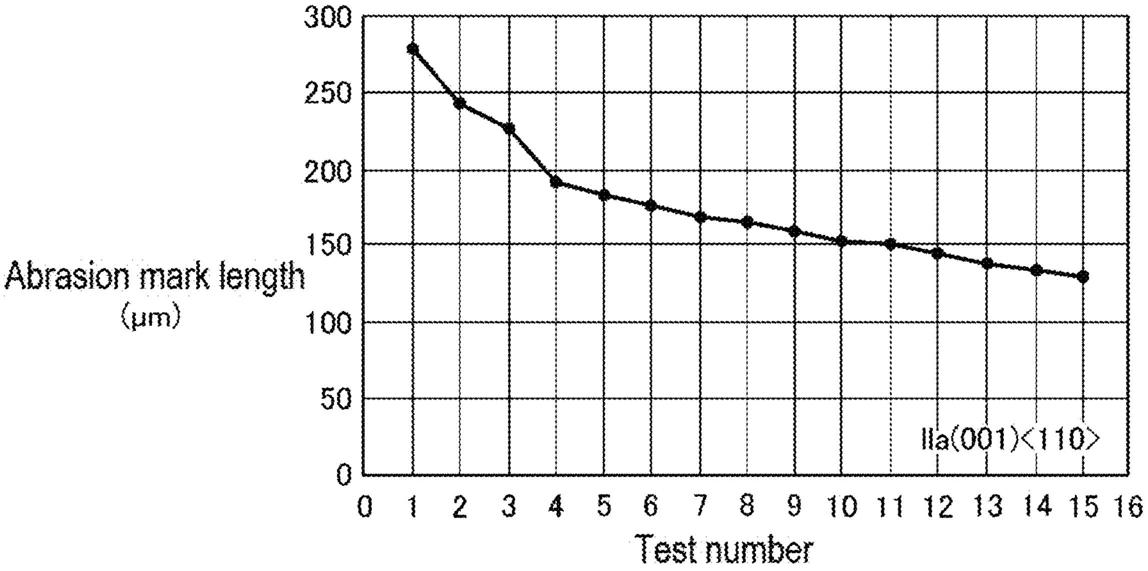
FIG. 9 is a graph showing the relationship between the test number and the abrasion mark length in the (001)<110> abrasion test of Example 2.
Figure 10:
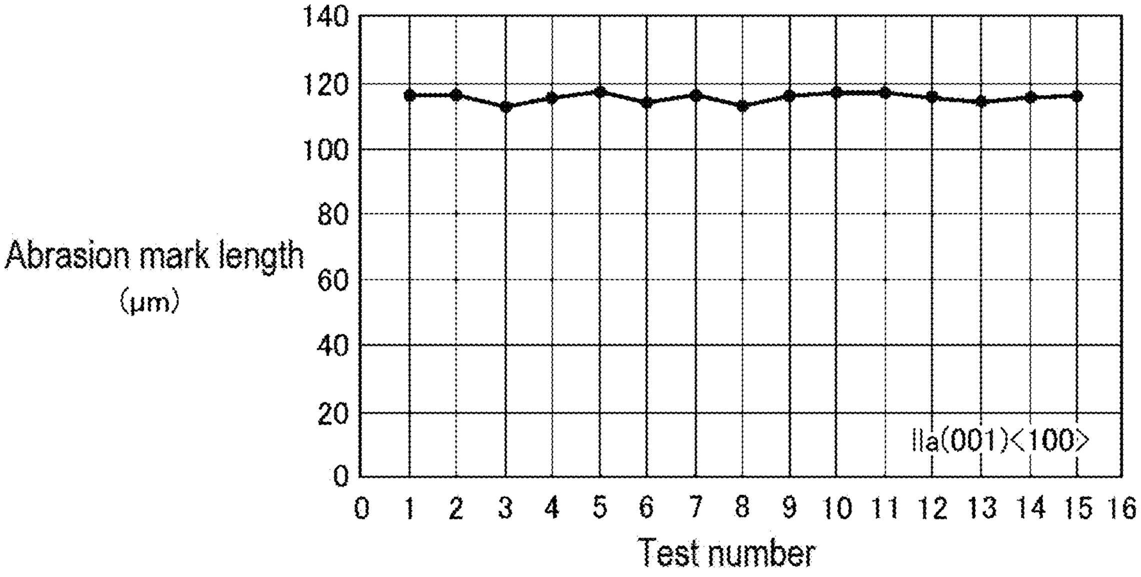
FIG. 10 is a graph showing the relationship between the test number and the abrasion mark length in the (001)<100> abrasion test of Example 2.

The result of the abrasion test (also referred to as "(001)<110> abrasion test" in the present description) of the (001) plane of the synthetic IIa type monocrystalline diamond in the <110> direction is shown in FIG. 9. The result of the abrasion test (also referred to as "(001)<100> abrasion test" in the present description) in the <100> direction of the (001) plane of the synthetic IIa type monocrystalline diamond is shown in FIG. 10. In the coordinate system of FIGS. 9 and 10, the horizontal axis represents the test number, and the vertical axis represents the length (μm) of the abrasion mark. The test number corresponds to the number of times of formation of the abrasion mark. For example, test number 5 means the fifth formation of the abrasion mark.

In the (001)<110> abrasion test, as shown in FIG. 9, the length of the abrasion mark is gradually shortened until the fourth abrasion mark is formed as shown by test number 4. Even after test number 5, the length of the abrasion mark is shortened by about 5 to 6 μm per one time. After the abrasion marks were formed 15 times as indicated by test number 15, the outer end portion was abraded and flattened, and the length D of the outer end portion in the rotation axis direction was 8 to 10 μm.

The reason why the length of the abrasion mark becomes shorter as the number of tests increases is presumed to be that the abrasion mark is easily formed because the outer end portion before the abrasion test is in a V shape and sharp state, and the outer end portion wears as the number of tests increases, and the abrasion mark is less likely to be formed.

In the (001)<100> abrasion test, as shown in FIG. 10, the length of the abrasion mark hardly changes.

From the above, it was confirmed that, for the purpose of examining the difference in abrasion resistance between crystals and the distribution state of the abrasion characteristic in a crystal, it is preferable to perform evaluation by forming the abrasion mark parallel to the <100> direction of the (001) plane of the monocrystalline diamond.

Example 3: Evaluation of Minute Abrasion Characteristic in <110> Direction of (001) Plane of Natural Ia Monocrystalline Diamond The contactor described in embodiment 1 was prepared as a contactor. The contactor has a cross-section shape shown in FIG. 3, and has the length r1 of 1.6 mm (a circle with a diameter of φ3.2 mm in top view), the angle θ of 120°, the length D of 5 μm, and a maximum length (thickness) 5 mm in rotation axis R direction.

Figure 11:
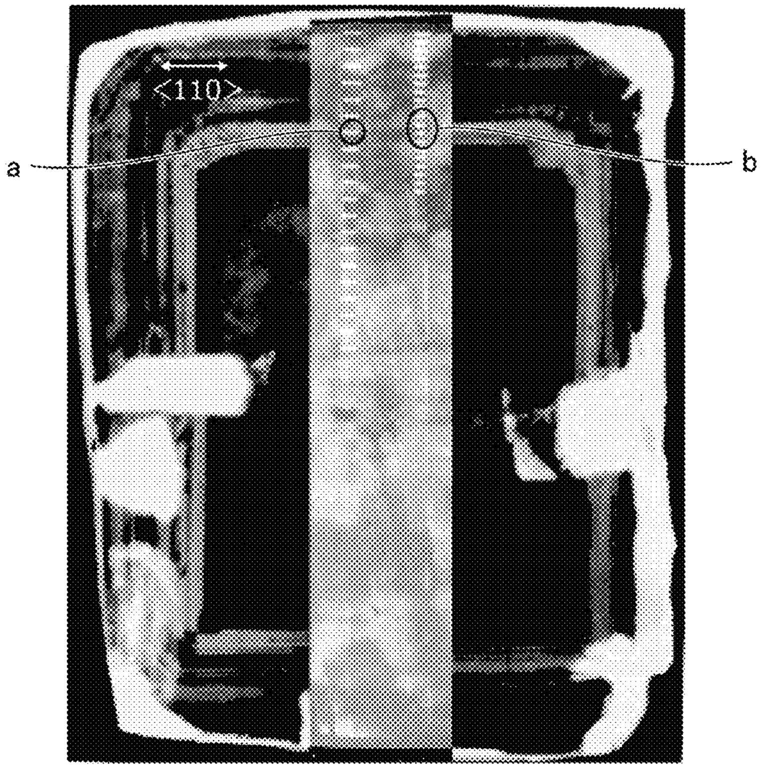
FIG. 11 is a photo substitutional view showing the ultraviolet-exited fluorescent image of the test piece of Example 3, on which an abrasion mark observed with an optical microscope is superimposed.

The contactor was installed in the abrasion testing apparatus shown in FIG. 6, and as shown in FIG. 11, abrasion marks were formed in parallel in the <110> direction of the (001) plane on a test piece made of natural Ia monocrystalline diamond, and the evaluation was performed. The conditions for forming the abrasion mark are: the rotational number 313 rpm of the contactor, pressing pressure 0.1 Mpa, and pressing time 1 minute per abrasion mark. The abrasion mark interval on the test piece was set to 100 μm (the abrasion marks in the left column of FIG. 11) in the formation of the first to twentieth abrasion marks from the start of the test, and was set to 50 μm (the abrasion marks in the right column of FIG. 11) in the formation of the twenty first to fortieth abrasion marks. The <110> direction of the (001) plane of the natural Ia monocrystalline diamond is identified based on a growth streak observed in an ultraviolet-exited fluorescent image of the natural Ia monocrystalline diamond.

Figure 12:
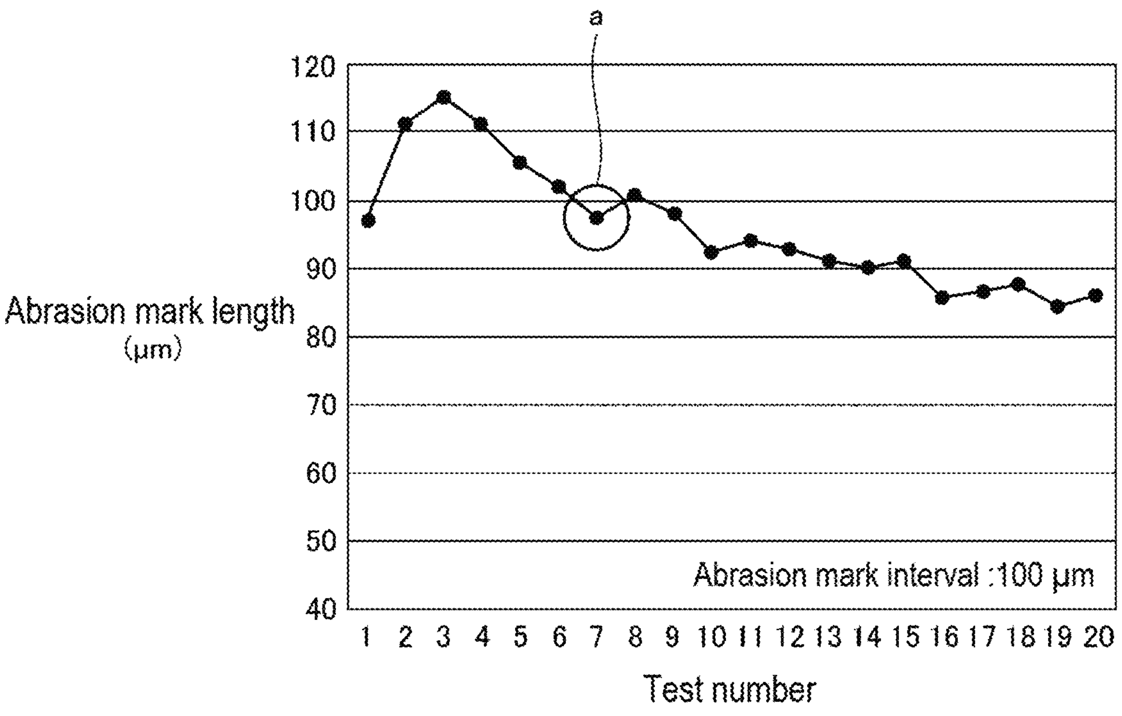
FIG. 12 is a graph showing the relationship between the test number and the abrasion mark length in the abrasion test at an abrasion mark interval of 100 μm in Example 3.
Figure 13:
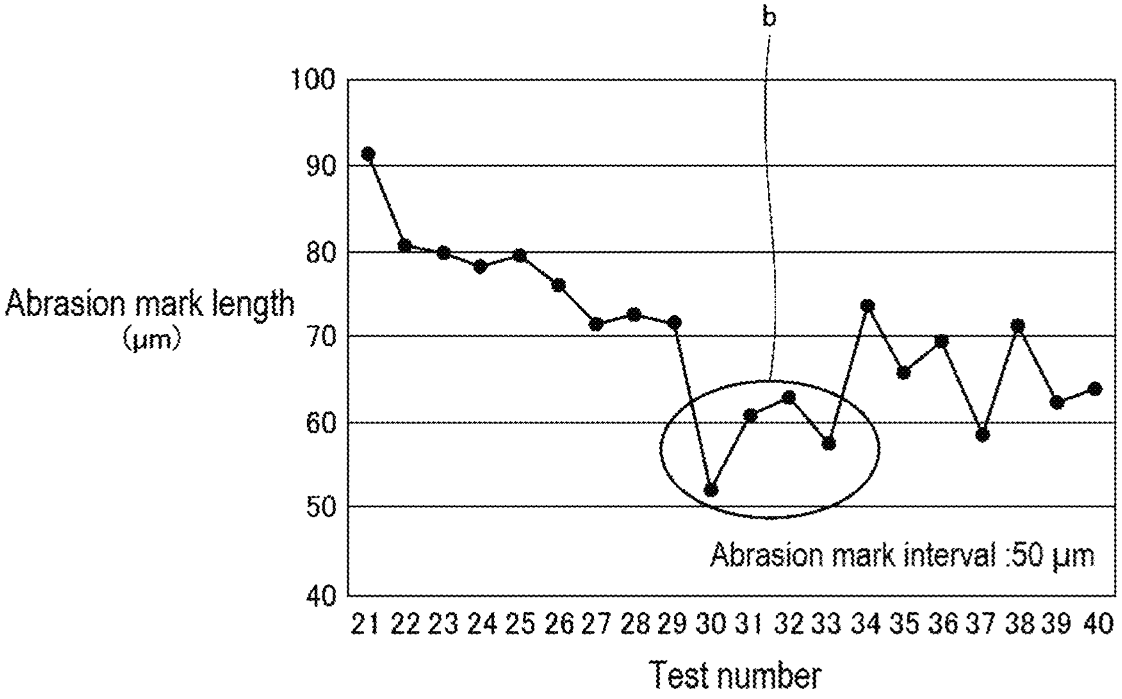
FIG. 13 is a graph showing the relationship between the test number and the abrasion mark length in the abrasion test at an abrasion mark interval of 50 μm in Example 3.

The result of the abrasion test at the abrasion mark interval of 100 μm is shown in FIG. 12. The result of the abrasion test at the abrasion mark interval of 50 μm is shown in FIG. 13. In the coordinate system of FIGS. 12 and 13, the horizontal axis represents the test number, and the vertical axis represents the length (μm) of the abrasion mark. The test number corresponds to the number of times of formation of the abrasion mark. For example, test number 5 means the fifth formation of the abrasion mark.

In the abrasion test with the abrasion mark interval of 100 μm, as shown in FIG. 12, the length of the abrasion mark is gradually shortened, but no clear change in the length of the abrasion mark was observed. The reason why the length of the abrasion mark is gradually shortened is presumed to be that the outer end portion wears with an increase in the number of tests, and thus the abrasion mark is less likely to be formed.

In the abrasion test with the abrasion mark interval of 50 μm, as shown in FIG. 13, the abrasion marks are rapidly shortened at the test numbers 30 to 33 in the ellipse indicated by reference symbol b. The abrasion marks of test numbers 30 to 33 are the abrasion marks in the ellipse indicated by reference symbol b in FIG. 11. In the ultraviolet-exited fluorescent image of the natural Ia monocrystalline diamond, a pale growth streak is observed in a portion indicated by a symbol b. From the above, it is confirmed that the part of the pale growth streak of the natural Ia monocrystalline diamond has high abrasion resistance.

In FIGS. 11 and 12, the abrasion marks shown in the ellipse of the symbol a correspond to the abrasion marks of the above-mentioned pale growth streak portion at the abrasion mark interval of 100 μm. When FIG. 12 and FIG. 13 are compared, the change in the length of the abrasion mark was more obvious in the case of the abrasion mark interval of 50 μm than in the case of the abrasion interval of 100 μm.

It was confirmed from Example 1 to Example 3 that, according to the evaluation method using the contactor of the present embodiment, the difference in the abrasion characteristic (characteristic relating to the original abrasion resistance of diamond) of the monocrystalline diamond due to the plane orientation and the like can be accurately evaluated even in the minute region of a level of several tens of micrometers.

Although the embodiments and examples of the present disclosure have been described above, it is originally intended that the configurations of the above-described embodiments and examples may be appropriately combined or variously modified. The embodiments and examples disclosed herein are illustrative in all respects and should not be construed as limiting. The scope of the present disclosure is defined by the appended claims rather than the foregoing embodiments and examples, and is intended to include all modifications within the scope and meaning equivalent to the appended claims.

REFERENCE SIGNS LIST

1 contactor
2 first portion
3 second portion
3A outer end portion
31 first surface
32 second surface
31A first boundary portion
32A second boundary portion
33 connection surface
R rotation axis
60 machining center
61 spindle
62 fixation screw
70 sample holding portion
71 air cylinder
72 linear guide
75 monocrystalline diamond
76 jig
77 plane

The invention claimed is:

1. A contactor having an annular shape and made of a polycrystalline diamond including a plurality of diamond particles, the contactor being configured to have a rotation axis extending through a center of the contactor, the contactor comprising:

a first portion having a constant thickness in a radial direction, the first portion including an inner end portion; and a second portion having a thickness decreasing in the radial direction, the second portion including an outer end portion, wherein the second portion has a first surface continuous with an upper surface of the first portion, a second surface continuous with a lower surface of the first portion, and a connection surface connecting the first surface and the second surface to each other and including the outer end portion, wherein, in a cross-section along the rotation axis, an angle θ formed by a first line segment indicating the first surface and a second line segment indicating the second surface is 100° to 150°, a length between a first boundary portion and a second boundary portion is 1 μm to 10 μm, the first boundary portion being a boundary between the first surface and the connection surface, the second boundary portion being a boundary between the second surface and the connection surface, and a length from the rotation axis to the outer end portion is 1 mm to 10 mm, and wherein an average particle diameter of the plurality of diamond particles is 0.1 μm to 100 μm.

2. The contactor according to claim 1, wherein Knoop hardness of the polycrystalline diamond is 45 GPa or more.

3. The contactor according to claim 1, wherein a line of intersection of the connection surface and a cross-section including the rotation axis is a straight line.

4. The contactor according to claim 1, wherein the length from the rotation axis to the outer end portion is larger than a length from the rotation axis to the first boundary portion and larger than a length from the rotation axis to the second boundary portion.

5. An evaluation method of an abrasion characteristic of a monocrystalline diamond in a minute region, the evaluation method comprising:

a first step of forming an abrasion mark on the monocrystalline diamond by, while rotating the contactor according to claim 1, pressing the monocrystalline diamond against the outer end portion of the contactor; and a second step of evaluating the abrasion characteristic of the monocrystalline diamond in the minute region based on a length of the abrasion mark.

6. The evaluation method according to claim 5, wherein the monocrystalline diamond has a plane, and wherein the first step includes a 1-1 step of disposing the monocrystalline diamond with the plane facing the contactor and being parallel to the rotation axis, and a 1-2 step of pressing the monocrystalline diamond against the outer end portion by applying a load in a normal direction of the plane to the monocrystalline diamond.

7. The evaluation method according to claim 6, wherein the plane of the monocrystalline diamond is a (001) plane, and wherein the abrasion mark is parallel to a <100> direction of the (001) plane.

* * * * *